United States Patent [19]

Sato et al.

[11] Patent Number: 5,118,679

[45] Date of Patent: Jun. 2, 1992

[54] AGENT FOR PREVENTING AND TREATING OPACITY OF LENS

[75] Inventors: Susumu Sato; Norihiro Kakimoto, both of Tokyo; Mikio Miyata, Kanagawa; Shigezo Uga; Kunie Nakamura, both of Kanagawa, all of Japan

[73] Assignees: Asai Germanium Research Institute Co., Ltd.; Sato Pharmaceutical Co., Ltd., Tokyo, Japan

[21] Appl. No.: 554,724

[22] Filed: Jul. 19, 1990

[30] Foreign Application Priority Data

Jul. 20, 1989 [JP] Japan ................... 1-187658
Dec. 29, 1989 [JP] Japan ................... 1-344590

[51] Int. Cl.$^5$ ................... A61K 31/535; A61K 31/28
[52] U.S. Cl. ................... 514/229.5; 514/492; 514/912
[58] Field of Search ................... 514/228.8, 229.5, 492

[56] References Cited

U.S. PATENT DOCUMENTS 4,296,123 10/1981 Ishikawa et al. ................... 514/492

FOREIGN PATENT DOCUMENTS

| | | |
|---|---|---|
| 0016444 | 10/1980 | European Pat. Off. |
| 0085513 | 8/1983 | European Pat. Off. |
| 1365997 | 9/1974 | United Kingdom . |
| 2080109 | 2/1982 | United Kingdom . |
| 2143128 | 2/1985 | United Kingdom . |
| 2190835 | 12/1987 | United Kingdom . |
| 2191697 | 12/1987 | United Kingdom . |
| 2211410 | 7/1989 | United Kingdom . |
| 2211411 | 7/1989 | United Kingdom . |
| 2213059 | 8/1989 | United Kingdom . |

*Primary Examiner*—Frederick E. Waddell
*Assistant Examiner*—Zohreh A. Fay
*Attorney, Agent, or Firm*—Burns, Doane, Swecker & Mathis

[57] ABSTRACT

The present invention is to provide a highly effective agent for preventing and treating opacity of lens, containing the organic germanium compound represented by the formula (1);

$$(Ge-\underset{\underset{R_2}{|}}{\overset{\overset{R_1}{|}}{C}}-\overset{\overset{R_3}{|}}{C}H-COX)_2O_3 \quad (1)$$

(wherein R1 to R3 represent hydrogen atoms, lower alkyl groups each of which may be the same or different and selected from the group consisting of methyl group, ethyl group, etc., or phenyl groups substituted or unsubstituted; X represents a hydroxyl group, an O-lower alkyl group, an amino group or $O-Y^+$ {Y represents a metal such as sodium, potassium, etc., or a compound having a basic group such as lysozyme and basic amino acid, etc.})or (2) a combination of the organic germanium compound and aminoguanidien, or (3) a combination of the organic germanium compound specifically defined above and the specific phenoxazine derivative.

26 Claims, 7 Drawing Sheets

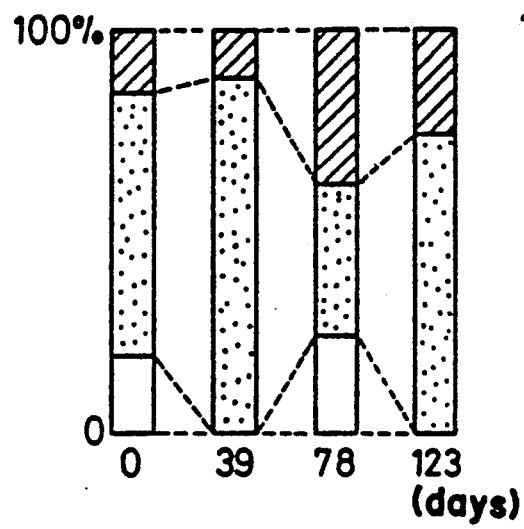
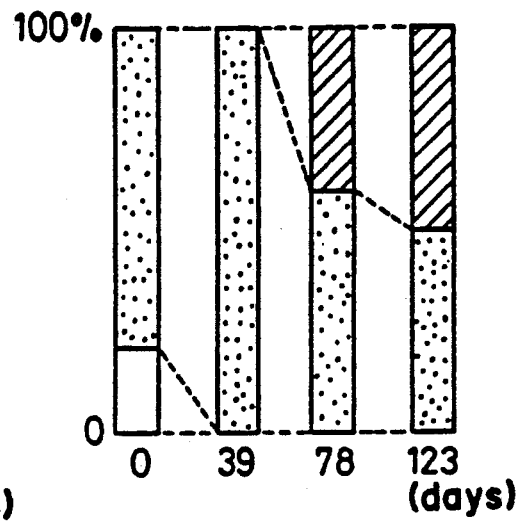
FIG. 3A Eye-drop group
FIG. 3B Control group
▨ Opacity
▦ Nucleus hardening
☐ Transparency

- Bovine serum albumin + D-glucose
- Bovine serum albumin
- Agent of the present invention added

- Control
- Agent of the present invention added

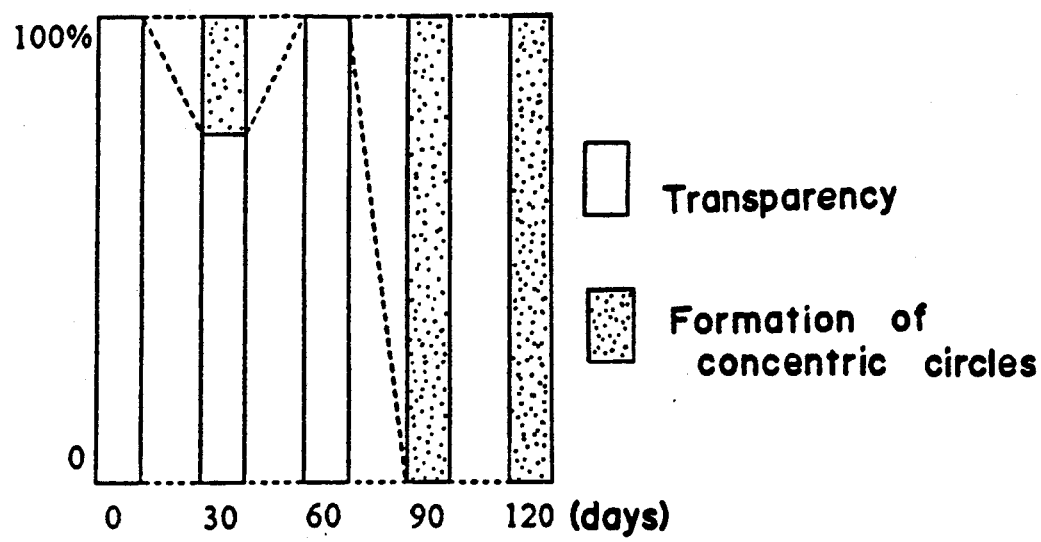
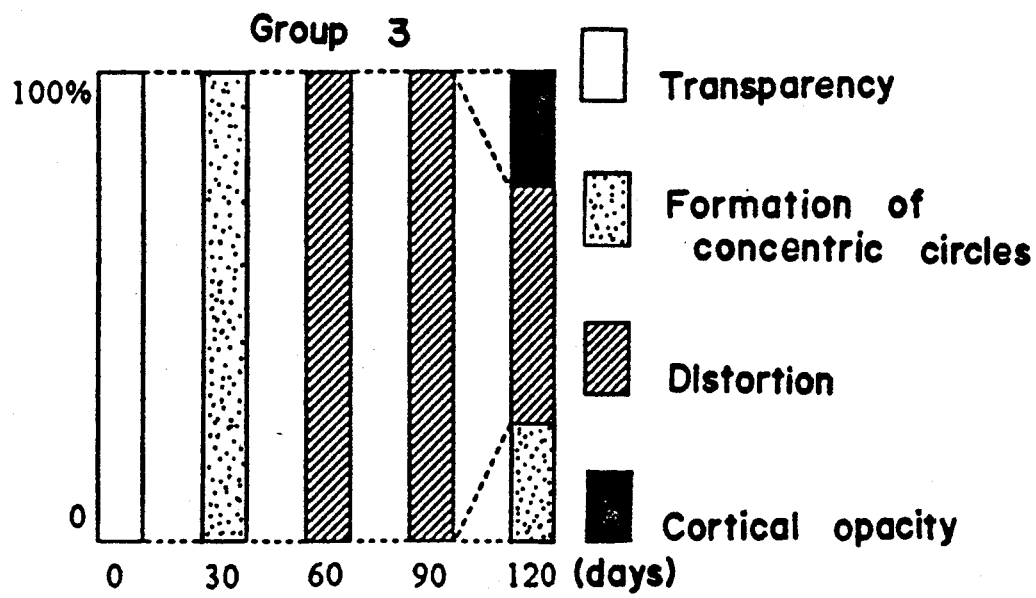

AGENT FOR PREVENTING AND TREATING OPACITY OF LENS

BACKGROUND OF THE INVENTION

1. Field of the Invention

The present invention relates to an agent for preventing and treating opacity of lens; more specifically, the present invention relates to an agent for preventing and treating opacity of lens, the agent comprising as effective ingredients specific organic germanium compound or the specific organic germanium compound together with aminoguanidine.

The present invention further relates to a highly effective agent for preventing and treating opacity of lens, the agent comprising a combination of a specific organic germanium compound and specific phenoxazine derivatives.

2. Prior Art

Lens of eyes is composed of as principle components about 65% of water and about 35% of protein, the ratio of protein contained in lens being higher than in other tissues. Under a variety of biological controls, than the protein in a high concentration, along with water inside cells, forms and maintains lens in hydrophilic colloidal state to retain transparency thereof. If lens which should be transparent happens to get opaque by some etiology, however, the quantity of light which reaches the retina decreases. Thus, visual acuity through the lens generally deteriorates, depending on the degree of opacity induced.

As the etiology of the incidence of opacity in the lens is diversified, it is quite difficult to discuss generally. One of the proposed mechanisms is such that the water-soluble, the membrane and the water-insoluble lens proteins described above, contain vast amounts of the SH group (thiol group), which are transformed into a S—S bond through a biological oxidative reaction, to form insoluble aggregated products, leading to the opacification of the lens. Another explanation is that the aforementioned proteins react with sugars non-enzymatically and irreversibly to form a reaction mixture called Amadori-products, of which reactions are general reactions between amino group of proteins and carbonyl groups of sugars, known as the Mailard Reaction. And this Mailard Reaction is considered to be a key reaction leading to aging. Such an explanation is considered to be one of the etiologies for causing opaque lenses.

The typical example of disease associated with an opaque lens is known as a cataract, which is classified into congenital cataract and an acquired one. The latter is further classified into senile cataract, traumatic cataract and diabetic cataract and others. In any type of cataracts, the formation of Amadori-products is considered to be a cause of lens opacities.

PROBLEMS THAT THE INVENTION IS TO SOLVE

One thing which is definitely clear in this field is that there has not yet been established any therapeutic treatment to prevent a opacity of a lens or reduce the opacity if it might happen.

That is, many problems have not yet been solved regarding opacification of lens, including cataract as explained above, so that specific agents for preventing or treating the opacity of a lens have not been developed. Thus, the agents for exerting significant effects only on recovering visual acuity or blocking the progress of opacification are now currently used.

SUMMARY OF THE INVENTION

The objective of the present invention is to provide an agent capable of efficiently preventing and treating opacity of a lens, on the basis of the prior art described above.

Another objective of the present invention is to provide an agent without toxicity or side effects, because such agents should be administered for a long period.

In order to achieve the above objectives, the present invention is constructed to provide an agent for preventing and treating opacity of a lens, the agent containing as the effective component the organic germanium compound represented by the formula;

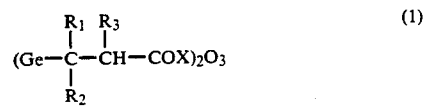

wherein $R_1$ to $R_3$ represent hydrogen atoms, lower alkyl groups each of which may be the same or different and selected from the group consisting of methyl group, ethyl group, etc., or phenyl groups substituted or unsubstituted; X represents a hydroxyl group, an O-lower ankly group, an amino group or $O^- Y^\pm$ {Y represents a metal such as sodium, potassium, etc., or a compound having a basic group such as lysozyme and basic amino acid, etc.}).

In order to achieve the above objectives, the present invention is constructed to provide an agent for preventing and treating opacity of lens, the agent containing a the effective components the organic germanium compound represented by the formula (1) together with aminoguanidine.

In order to achieve the above objectives, the present invention is further constructed to provide an agent for preventing and treating opacity of lens, the agent containing as the effective components the organic germanium compound represented by the formula (1) and specific phenoxazine derivatives.

BRIEF DESCRIPTION OF DRAWINGS

FIG. 3A and B is a diagram showing the percentage distribution of lens symptoms.

FIGS. 8 through 13 show the percentage distribution of lens symptoms in each eye drop group.

FIGS. 8 through 10 show the results of administration of the eye drop containing the present agent to the mice aged 1 month and thereafter.

FIGS. 11 through 13 show the results of administration of the eye drop containing the present agent to the animals aged 5 months and thereafter.

DETAILED DESCRIPTION OF THE INVENTION

Figure 1:
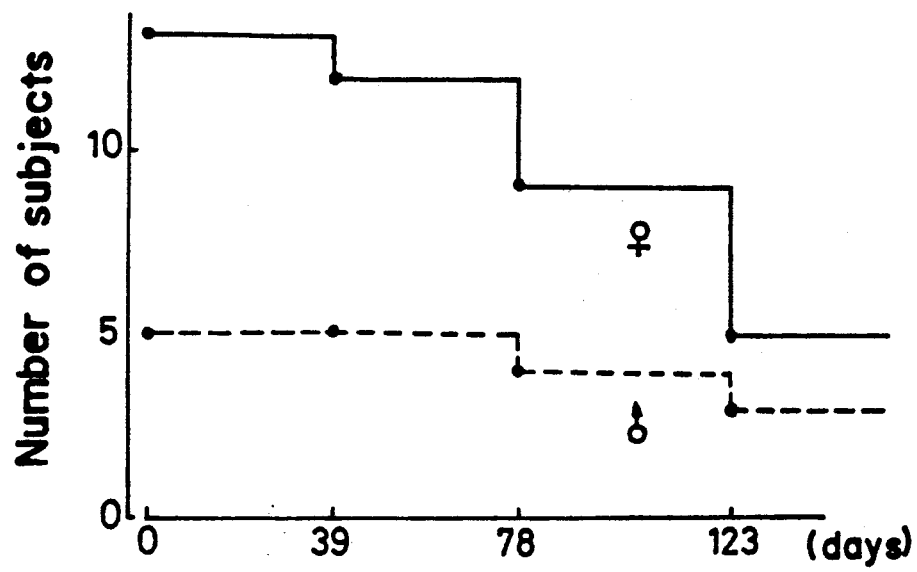
FIG. 1 is a graph showing the survival status of senile accelerated mice.

The present invention will now be explained in detail hereinafter.

The agent for preventing and treating opacity of lens contains as the effective component the specific organic germanium compound represented by the formula (1);

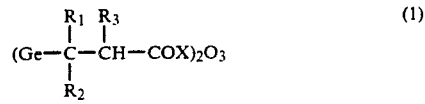
(1)

Explanation about the compound will be made first.

The principle structure of the compound is composed of germylpropionic acid where a germanium atom is bonded to a propionic acid derivative having three substituents $R_1$ to $R_3$ and a functional group containing oxygen, i.e. OX, and the germanium atoms of the principle structure and the oxygen atoms are bonded in the ratio of 2:3.

Each of the substituents $R_1$ to $R_3$ herein represents a hydrogen atom, a so-called lower alkyl group such as a methyl group, ethyl group, propyl group, butyl group, etc., or a phenyl group substituted or unsubstituted; the substituent X represents a hydroxyl group, an O-lower alkyl group, an amino group or $O^-Y^\times$ representing the salt of carboxylic acid, individually. Substituent Y represents a metal such as sodium, potassium or the like (the metal is not necessarily monovalent), or a basic compound represented by basic amino acid and the like, such as lysozyme or lysine.

The substituents $R_1$ and $R_2$, and the substituent $R_3$ are bonded to the germanium atom at $\alpha$ and $\beta$ positions, respectively. Thus, the examples of the organic germanium compound to be used in accordance with the present invention are illustrated as follows;

$(Ge-CH_2-CH_2-COOH)_2O_3$ (1-1)

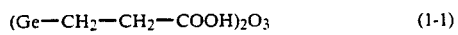
(1-2)

(1-3)

(1-4)

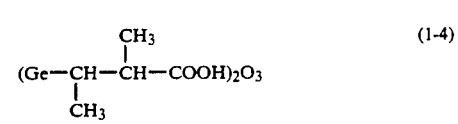
(1-5)

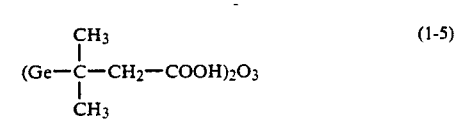
(1-6)

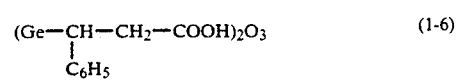
(1-7)

$(Ge-CH_2-CH_2-COOCH_3)_2O_3$ (1-8)

$(Ge-CH_2-CH_2-CONH_2)_2O_3$ (1-9)

$(Ge-CH_2-CH_2-COO^-Na^+)_2O_3$ (1-10)

The organic germanium compounds having the above structure may be produced in various processes.

For examples, the compound wherein X is OH in the formula (1) may be produced as shown in the following reaction formula:

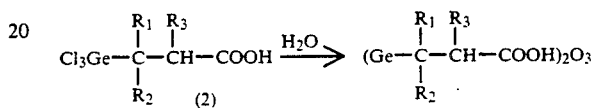

That is, trihalogermylpropionic acid in which the substituents $R_1$ to $R_3$ are preliminarily introduced, such as trichlorogermylpropionic acid (2) and the like, may be hydrolyzed.

On the other hand, the compound wherein X is O-lower alkyl group may be obtained, for example, by reacting thionyl chloride, etc. with the above compound (2) to transform the compound into the corresponding acid halide and subsequently reacting alcohol corresponding to the above O-lower alkyl group, followed by hydrolysis of the resulting compound. And the compound of the formula (1) wherein X is $NH_2$ may be obtained, for example, by reacting ammonia to the above acid halide, followed by the hydrolysis.

The compound of the formula (1) containing $COO^-Y^\pm$ group as substituent X, wherein Y is a metal may be obtained, for example, by reacting metal hydroxide with the above compound (1), while the compound containing a basic group as Y may be subjected to known acid-base reaction.

The organic germanium compounds obtained in the above manner are subjected to instrumental analysis for nuclear magnetic resonance (NMR) and infrared absorption (IR) spectra, and the results strongly support that the above compound can be represented by the above formula (1).

The above formulas represent the organic germanium compounds in crystalline state, which are hydrolyzed in aqueous solution at germanium-oxygen bonding. For example, the above compound (1—1) transforms its original structure into the following structure;

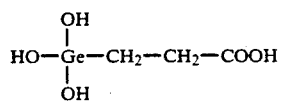

Among the above compounds, the compound (1—1) may be preferable because of its easy availability.

Aminoguanidine to be used in the present invention is represented by the following formula;

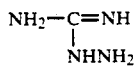

and is one of the compounds known as strong nucleophilic reagents.

The phenoxazine derivative to be used in accordance with the present invention is represented by the following principle structural formula;

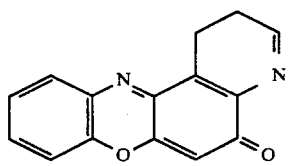

and more specifically, 1-hydroxy-5-oxo-5H-pyrido(3,2-a)phenoxazine-3-carboxylic acid (general name; pyrenoxine) of the following formula;

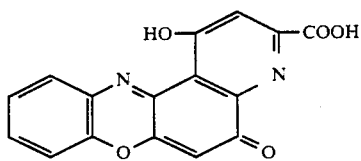

or its salt with metal such as sodium, potassium and the like may be preferable.

This compound has been conventionally used for treatment of cataract. The outcome of such treatment has been reported in academic papers (For example, see Japanese Clinical Ophthalmology 11:272, 1957).

The other phenoxazine derivatives represented by the above principle structural formula are publicly disclosed in Japanese Patent Publication No.10570/1980.

The agent for preventing and treating opacity of lens in accordance with the present invention contains as the effective component the organic germanium compound synthesized in the above manner, or the organic germanium compound along with the aforementioned aminoguanidine, or the organic germanium compound with the phenoxazine derivative described above; they may be prepared as an eye drop, preferably, together with known components such as boric acid, sodium chloride, sodium hydroxide, or benzalkonium chloride, s-aminocaproic acid, methyl p-oxyaminobenzoic acid, and chlorobutanol.

The solubility of the organic germanium compound and the like as the effective components of the present invention may increase in a basic eye drop.

Since the organic germanium compound as the effective component of the present invention has characteristic features such as extremely low toxicity and little side effects, the amount thereof to be used in an eye drop may be determined in a relatively free manner. The amount will be illustrated in the range of, for example, 0.5 to 5% of the total amount of eye drop. Alternatively, for the eye drop containing as the principle agents the organic germanium compound and aminoguanidine, the organic germanium compound is used in the range of, for example, about $10^{-5}$ to $10^{-7}$ of the aminoguanidine content.

The eye drop containing as the principle agents the organic germanium compound and the phenoxazine derivative may be prepared so that 5-500 mg of the organo-germanium compound and 0.05-0.5 mg of the phenoxazine derivative may be contained in 1 ml of the eye drop.

Phenoxazine derivatives have been used for treatment of cataract for a long time and therefore, the safety thereof has been evaluated and verified.

Furthermore the agent containing the organic germanium compound and the agent containing a phenoxazine derivative may be separately prepared in advance, and then they may be mixed to prepare the agent of the present invention on an as needed basis.

ADVANTAGES OF THE INVENTION

The testing of the effects of the agent of the present invention in senile accelerated mice susceptible to the opacity of a lens, indicates such effects as the decrease in the number of opaque eyes and the increase in the number of transparent eyes, due to the eye drop containing the agent of the present invention.

The in vitro experiments using a crystalline from bovine lens and glucose demonstrate the effects such that the present agent containing as the effective component the organic germanium compound described above or containing the organic germanium compound and aminoguanidine may prevent opacification of a lens or reduce opacity in a lens, by suppressing Amadori-products formation and decomposing the Amadori-products once formed into lower-molecular substances.

EXAMPLES

The present invention will now be explained in the following embodiments.

EXAMPLES 1

(1) Procedure 18 senile accelerated mice of 10 months (5 males and 13 females) were divided into 2 groups; a group consisting of 10 mice was administered with one drop of the eye drop, the agent of the present invention which contained the organic germanium compound (1.1) in a ratio of 4 %, 4 times daily, 6 days/week over 123 days, while the other group consisting of 8 mice was used as controls without eye drop. The both groups were kept and fed under the same conditions. Lenses of each subject were examined by a microscope while the subject was under the anesthesia of 0.7 ml/kg sodium nembutal intraperitoneally injected. The examination was carried out four times, namely prior to the initiation of the experiments and 39, 78, 123 days after the initiation.

(2) Results

Survival of senile accelerated mice

Prior to the initiation of the experiments, the number in FIG. 1. The total number of survivals showed gradual decrease up to the age of 12 months, i.e. the decrease by 1 on day 39, and by additional 5 on day 78. However, the number of survivals showed rapid decrease by the age of 14 months corresponding to day 123. That is, the total survival number decreased by half or more.

Figure 2:
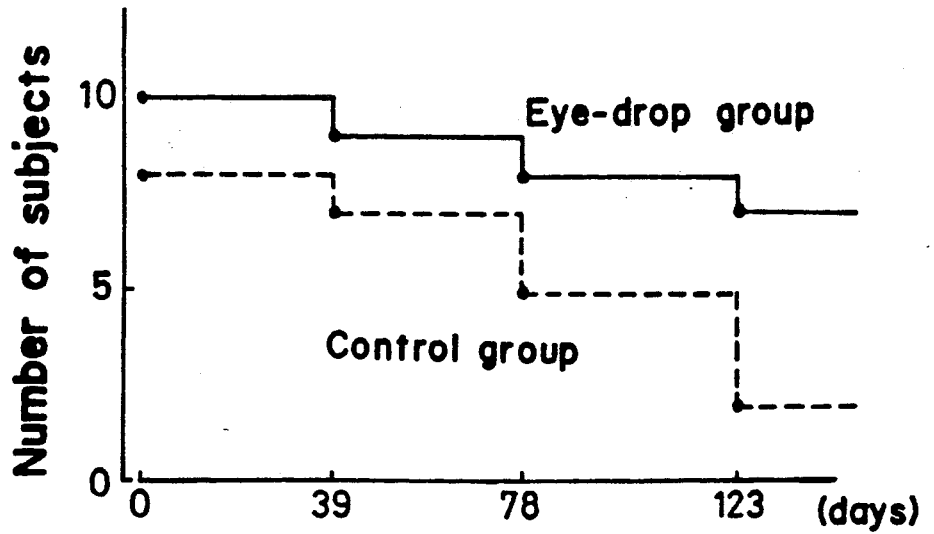
FIG. 2 is a graph showing comparison of the survival status between an eye drop group and a control group.

The survival on day 123 was compared between the eye drop group and the control group. As is shown in FIG. 2, 3 deaths in 10 mice were observed in the eye drop group, while 6 deaths in 8 were observed in the control group. Therefore, it was clearly demonstrated that the eye drop group had a longer survival.

Lens symptoms of senile accelerated mice and survival status

Lenses of senile accelerated mice of age 10 months were subjected to microscopic examination. Consequently, a subjective difference was observed in the incidence of the opacification of the lenses. The opaque conditions of lenses were classified into three types, namely transparency, nucleus hardening and opacity. Transparent lens does not have any abnormal symptoms so that retinal vessel may be ob served through; In a lens diagnosed as having nucleus hardening, nucleus hardening was extending into the cortical intermediate layer, followed by concentric circles in the form of light waves on the polar surface. Histologically, a certain boundary layer with different staining properties was observed between the nucleus surrounding region and the cortical surface layer, and recessive or protrusive portions of various sizes were observed at the site of concentric circles.

The diagnosis of opaque lens was established, based on the observation of the occurrence of opacity in the axle form on normal cortex. Among them, severe opaque lenses could not be observed by 78 days after the initiation of the experiments.

Effects of the accent of the present invention through eye drop

TABLE 1 below shows the lens observations in the eye drop group and the control group, before the initiation of the experiments and on days 39, 78 and 123 after the initiation.

TABLE 1

|  | 0 | 39 | 78 | 123 | days |
|---|---|---|---|---|---|
| Dose group | | | | | |
| Transparency | 3 | 0 | 4 | 0 | eyes |
| Nucleus hardening | 13 | 16 | 6 | 9 | |
| Opacity | 4 | 2 | 6 | 3 | |
| Control group | | | | | |
| Transparency | 3 | 0 | 0 | 0 | eyes |
| Nucleus hardening | 11 | 12 | 6 | 2 | |
| Opacity | 0 | 0 | 4 | 2 | |

FIG. 3 shows the percentages of the above lens observations. In the eye drop group, the ratio of opaque lens was 20% before eye drop but it decreased to 11 %; the ratio of transparent lens was 15% before eye drop but it decreased to 0 on day 39, and subsequently it increased to 38 % on day 78. As described above, the effects of the eye drop of the agent of the present invention are clearly demonstrated.

On the contrary, the ratio of transparent eyes in the control group decreased while the ratio of opaque eyes increased, as the progress of their age. The exacerbation of the symptoms are remarkable.

Figure 4:
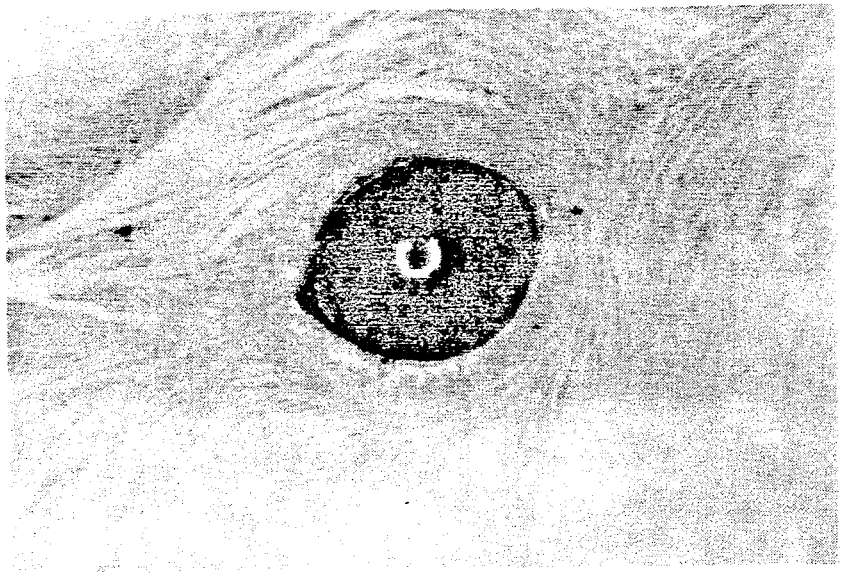
FIG. 4 is a photograph of an opaque lens of an animal prior to the treatment of eye drop.
Figure 5:
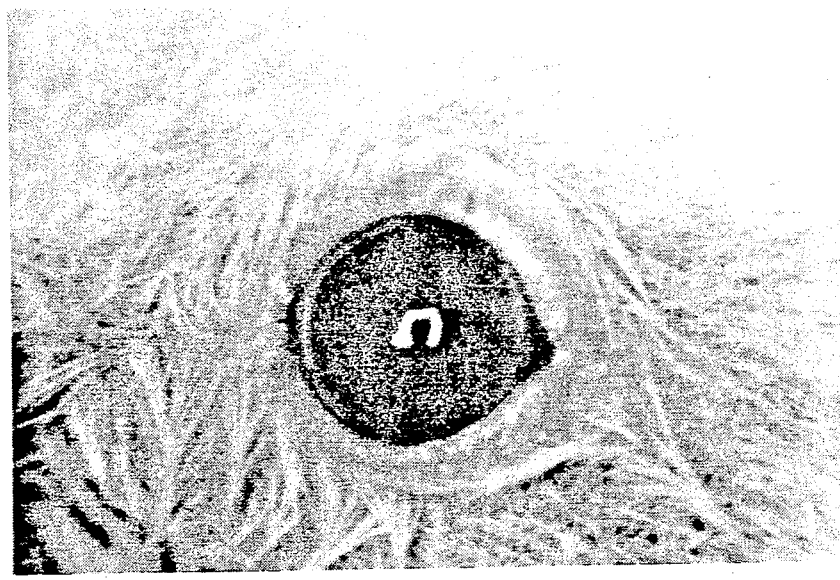
FIG. 5 is a photograph of the status of the same lens of the animal in FIG. 4, one month after the eye drop treatment.

FIGS. 4 and 5 show the comparison of the effects of the agent of the present invention in the same eye sample. The lens in FIG.4 shows slight opacity, but the lens one month later in FIG.5 shows considerable improvement concerning transparency.

Furthermore, the symptoms were locally improved due to the eye drop, such as the decrease in a number of concentric circles which were observed in the lens diagnosed nucleus hardening, and the decrease in the change in the equatorial bow construction because of aging.

EXAMPLE 2

(1) Procedure

Procedure using bovine α-crystalline

Equal amounts of 20mg/ml α-crystalline obtained from bovine lens (manufactured by Sigma Co.) and 200mM D-glucose were mixed, and 100μl of the resulting mixture was poured into a 96-well microtiter plate. To each of these wells, the solution of 200mM aminoguanidine chloride and 20mM organic germanium compound (1 1) described above were added, with diluting 5 -fold per each dilution, by using the box titration method. The 7-82 1 portion of the solution was taken from a well over scheduled time, and diluted with 133μl of 50mM phosphate buffer. Then, the diluted solution was applied on a TSK-G3000SW column equipped with a high-performance liquid chromatography system, to which a fluorescence detector for 350nm excitation wave length and 440nm fluorescence wave length, as well as an ultraviolet detector for 280nm were connected, for simultaneous detection.

In such manner, the Amadori-products product formed with α-crystalline and D-glucose was collected and washed, followed by resuspension in 0.5 mol phosphate buffer and redivided into a 96-well microtiter plate, in order to examine the effects of the organic germanium compound (1.1) and aminoguanidine.

Procedure using bovine serum albumin

Equal amounts of 200 mg/ml bovine serum albumin in 0.5 M phosphate buffer (PH 7.4) and 400mM D-glucose were mixed, to which was added 3mM NaN3. Aminoguanidine and the organic germanium compound (1.1) described above were adjusted of their concentrations to various given concentrations, separately, according to the box titration method and then, they were added to the above solution. Employing fluorescence intensity as an indicator, their effects on Amadori-products formation were examined. Alternatively, a mixture of bovine serum albumin and D-glucose was heated at 37° C. for a long period to produce Amadori products. The addition of the organic germanium compound (1—1) and aminoguanidine was carried out during the heating process and measurement was subsequently made over time to evaluate the effects by high-performance liquid chromatography.

(2) Results

Procedure using bovine α-crystalline

Although a dose of aminoguanidine alone at a lower concentration rather promoted Amadori-products formation, it was clearly demonstrated that the agent of the present invention containing the organic germanium compound (1—1) from a lower concentration to a higher one was effective on suppression of the Amadori-products formation. Furthermore, the agent of the present invention containing the organic germanium compound (1—1) and aminoguanidine suppressed the promoted Amadori-products formation which was observed in the group given aminoguanidine alone. In addition, the degree of Amadori-products formation was lower over the entire range of the concentrations in the above group than in the positive controls.

A dose of aminoguanidine alone of 40mM or 200mM was effective on reversible solubilization of Amadori-products produced by α-crystalline. The agent of the present invention containing the organic germanium compound (1—1) at a 20mM concentration, and the agent of the present invention containing the organic germanium compound (1—1) and aminoguanidine, as low as 800μM and 320μM, respectively, were effective.

The results are partly shown in TABLE 2.

The figures in TABLE 2 represent the integral values of fluorescence intensity measured by a fluorescence detector for 350nm excitation and 440nm fluorescence wave length.

TABLE 2

|  |  | Aminoguanidine hydrochloride (mM) | |  |
|---|---|---|---|---|
|  |  | 0 | 4 | 20 |
| Compound | 0 | 825* | 812 | 368 |
| (1-1) | 0.010240 | 407 | 352 | 263 |
| (μM) | 0.051200 | 321 | 390 | 232 |

The value obtained by α-crystalline alone was 137. The value marked with asterisk * was obtained in case when D-glucose was added to α-crystalline.

Procedure using bovine serum albumin

It was confirmed that bovine serum albumin and D-glucose dose formed Amadori-products of a fluorescence intensity exceeding 4-104 for 50 days. The experimental system was examined by high-performance liquid chromatography, and the results show remarkable increase in dimers or trimers of serum albumin.

Figure 6:
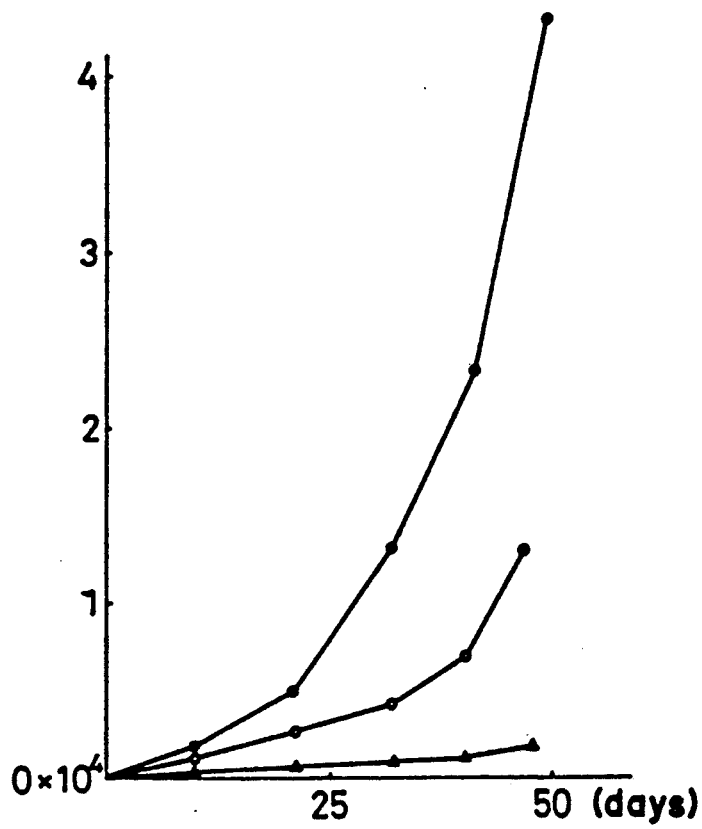
FIG. 6 is a graph showing the progress of Amadori-products formation from bovine serum albumin and D-glucose, and the effect of the agent of the present invention on the Amadori-products formation from bovine serum albumin and D-glucose.

To the system were added the agent of the present invention containing the organic germanium compound (1—1) (4mM) and aminoguanidine (200mM), which produced a significant suppression on Amadori-products formation. According to the results, the cooperative action between the organic germanium compound (1.1) and aminoguanidine was confirmed. The results are shown in FIG. 6. The experimental system was subjected to analysis by high-performance liquid chromatography, and the peaks corresponding to dimers and trimers of serum albumin got lower while a peak of lower-molecular substances appeared.

Figure 7:
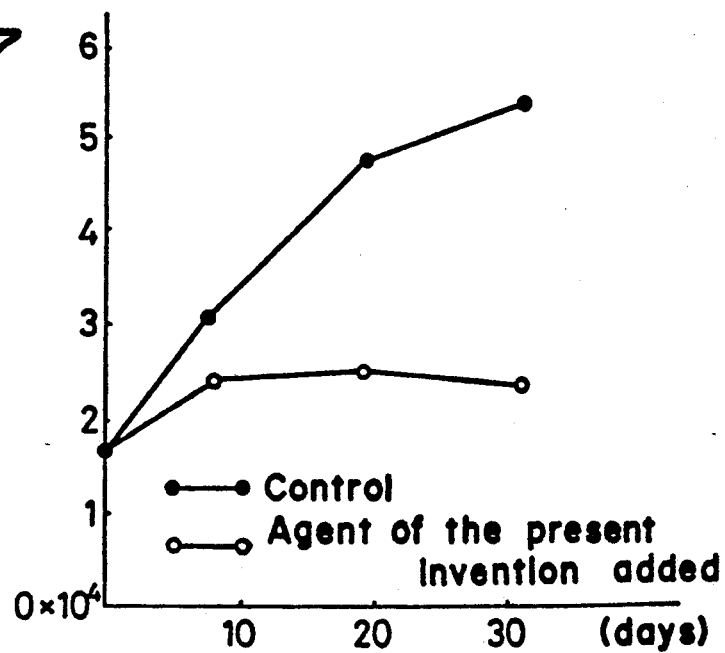
FIG. 7 is a graph showing the effect of the agent of the present invention on the Amadori-products formed from bovine serum albumin and D-glucose.

A mixture of bovine serum albumin and D-glucose were heated at 37° C. for 9 weeks to produce a sufficient amount of Amadori-products, to which was added the agent of the present invention containing the organic germanium compound (1—1) (20mM) and aminoguanidine (200mM). As is shown in FIG. 7, significant suppression on Amadori-products formation was observed, which indicates the presence, also in this system, of the cooperative action between the organic germanium compound (1—1) and aminoguanidine.

When the system was subjected to analysis by high-performance liquid chromatography, the peak corresponding to trimers of serum albumin became principle, while the peak of lower molecular substances, showing an intense ultraviolet absorption peak as well as decreased fluorescence appeared. These results indicate that the Amadori-products formation was disordered and that the constituting proteins were transformed into lower-molecular substances.

EXAMPLE 3

As for experimental animals, senile accelerated mice aged 1 month (12 mice) and 5 months (12 mice) were used. Both of the age groups were divided into three groups, individually; Group 1 was given the solution of 0.05 mg/ml 1. hydroxy-5-oxo-5H-pyrido(3,2.a)phenoxazine-3-carboxylic acid (general name; pyrenoxine) (the solution was referred to as pyrenoxine solution hereinafter); Group 2, both of the 4% organic germanium compound (1—1) solution (referred to as Ge solution) and pyrenoxine solution; Group 3 as the control group, distilled water containing a suppressive agent on surface activity as a placebo solution. The administration was carried out through eye drop, 4 times daily, 6 days /week. Before the initiation of eye drop, and 30, 60, 90 and 120 days after the initiation, mydriasis was induced using Midorin P (product name) in each subject under the anesthesia of 0.7ml/kg of sodium nembutal intraperitoneally injected, before subjecting to lens observation under a stereomicroscope.

The lens observation in senile accelerated mice may be roughly classified into 4 items, i.e. transparency, formation of concentric circles, distortion and cortical opacity in this example. By the term "transparency" is meant no abnormal symptom in lens so that retinal vessel can be observed through; by the term "formation of concentric circles" is meant 2 to 5 rings are observed in concentric circles in a lens; by the term "distortion" is meant the incidence of distortion in image on eyegrounds, because of abnormal refraction of lens; by the term "cortical opacity" is meant the incidence of wedge like or diffuse opacity. Two of such symptoms, formation of concentric circles and distortion were occurred in some lenses and in that cases, the symptom showing stronger change was selected as an abnormal symptom.

1. The eye drop experiments starting at 1 month since birth

The eyes of senile accelerated mice of age 1 month were examined prior to the administration of the eye drop. Most of the eyes including those of the control group had transparent lenses without any abnormal symptoms; mild cortical opacity and no eye anophthalmia was simultaneously observed in one subject of Group 2 (a simultaneous administration group of Ge solution and pyrenoxine solution).

The examination which was carried out on day 30 after the initiation of eye drop demonstrated that the cortical opacity observed prior to the initiation of eye drop disappeared. However, there occurred ring-like concentric circles in one eye of Group 1 (pyrenoxine administration group), one eye of Group 2 (a simultaneous administration of Ge solution and pyrenoxine solution) and two eyes of Group 3 (as the control group). The examination on day 60 after the initiation of eye drop demonstrated that abnormality in lens such as formation of concentric circles and distortion was observed in one eye of Group 1 and four eyes of Group 3.

The examination on day 90 after the initiation of eye drop demonstrated that the six eyes with transparent lens of Group 1, showed formation of concentric circles (in 4 eyes) and distortion (in two eyes), which indicated the occurrence of cataract at initial stage. Of Group 3, four eyes with distorted lenses did not propose any change from the symptoms observed at the prior examination. On the contrary, lenses of Group 2 were in good condition so that the lenses were thus diagnosed transparent.

The examination on day 120 after the initiation of eye drop demonstrated that distortion which was observed in two eyes of Group 1 on day 90 disappeared. Distortion disappeared in one of the four lenses of Group 3, which had been diagnosed to be in distorted state. Such results indicate that distortion inlens may not generally be fixed. Of Group 2, one animal died during the experiments, but all of the other remaining mice were judged normal at this examination.

Figure 8:
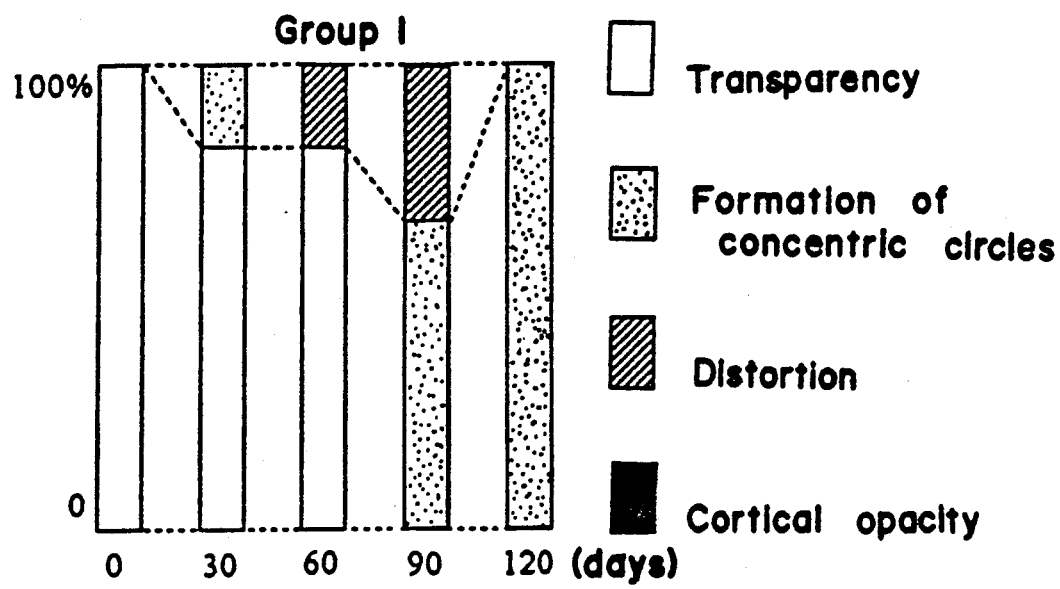
Figure 9:
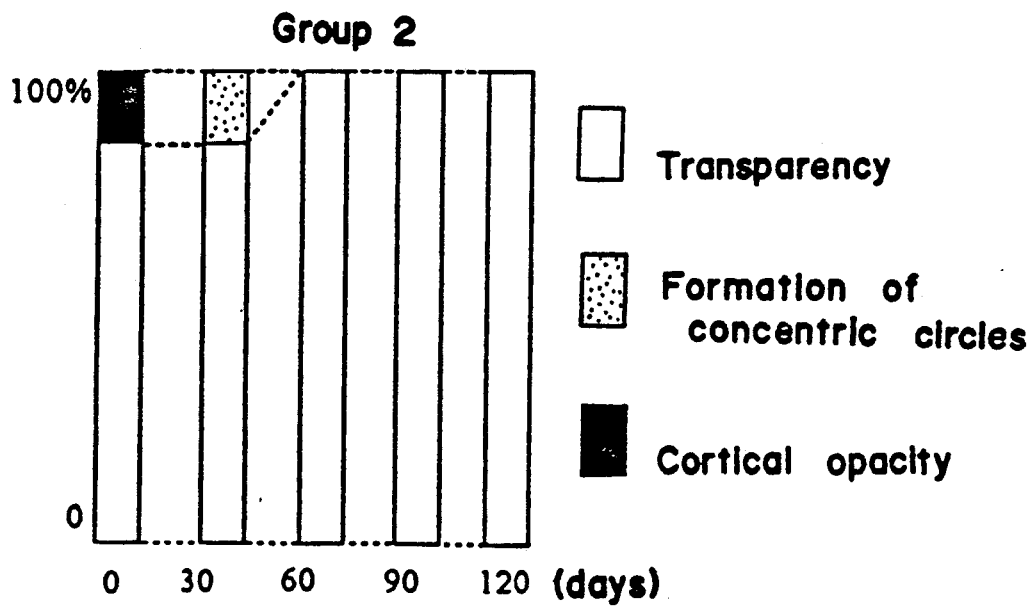
Figure 10:
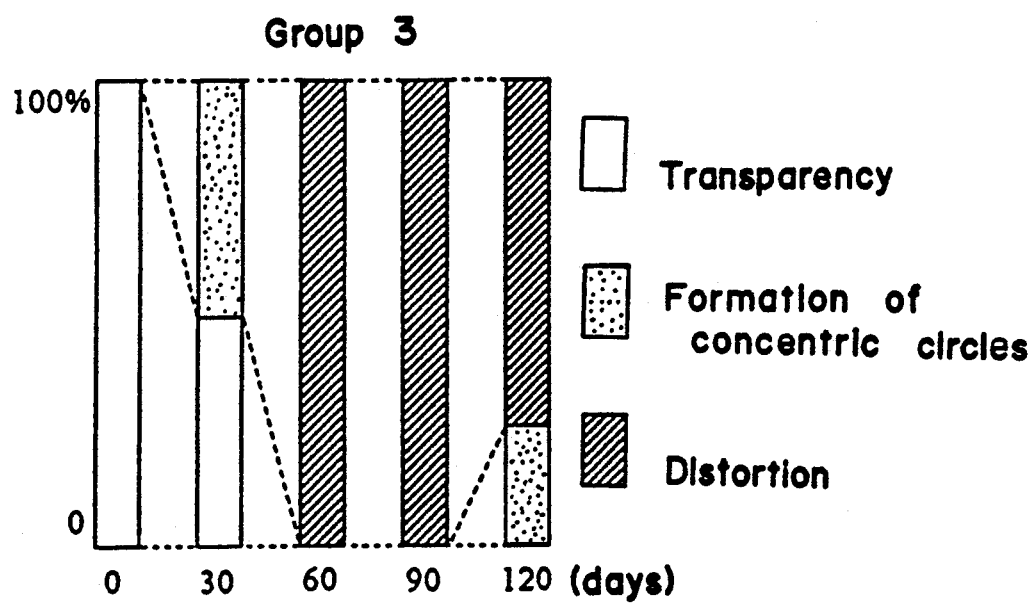

The results heretofore mentioned are shown in TABLE 3 below. The ratios of each symptom to total are shown in FIGS. 8 through 10.

It might be said that these experiments verify the preventive effect of the agent of the present invention.

ever, the occurrence of cortical opacity was observed in a different eye, indicating the further progress of cataract.

Figure 11:
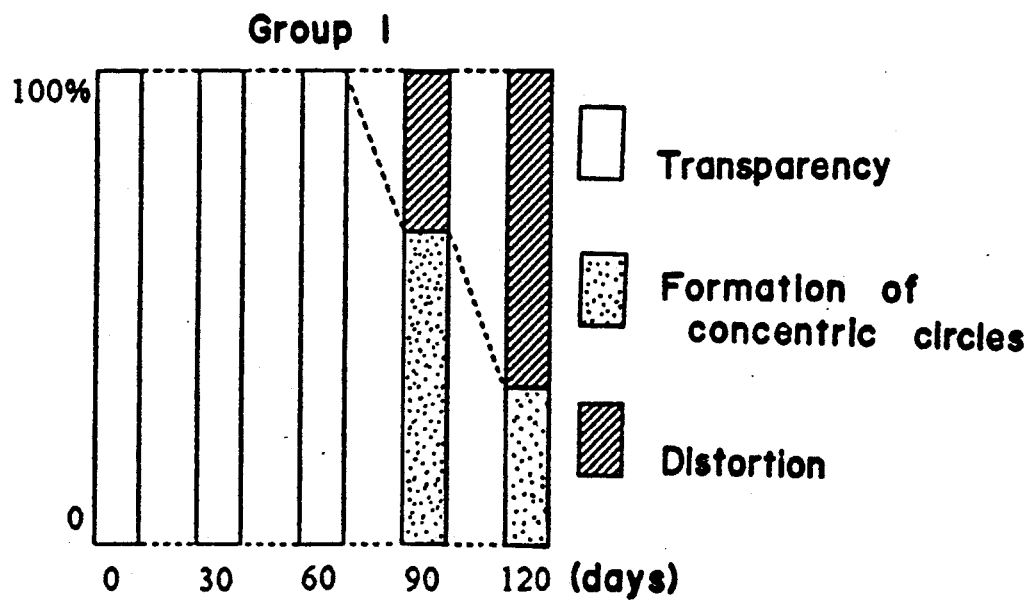

The results heretofore mentioned are shown in TABLE 4 below. The ratios of each symptom to total are shown in FIGS. 11 through 13.

It might be said that these experiments verify the effects of the agent of the present invention, on preventing the progress and the treatment

TABLE 3

| Symptoms | Before eye drop initiation | | | On day 30 | | | On day 60 | | | On day 90 | | | On day 120 | | |
|---|---|---|---|---|---|---|---|---|---|---|---|---|---|---|---|
| Dose group | 1 | 2 | 3 | 1 | 2 | 3 | 1 | 2 | 3 | 1 | 2 | 3 | 1 | 2 | 3 |
| Number of eyes | 6 | 7 | 4 | 6 | 7 | 4 | 6 | 7 | 4 | 6 | 7 | 4 | 6 | 5 | 4 |
| Transparency | 6 | 6 | 4 | 5 | 6 | 2 | 5 | 7 | 0 | 0 | 7 | 0 | 0 | 5 | 0 |
| Formation of concentric circles | 0 | 0 | 0 | 1 | 1 | 2 | 0 | 0 | 0 | 4 | 0 | 0 | 6 | 0 | 1 |
| Distortion | 0 | 0 | 0 | 0 | 0 | 0 | 1 | 0 | 4 | 2 | 0 | 4 | 0 | 0 | 3 |
| Cortical opacity | 0 | 1 | 0 | 0 | 0 | 0 | 0 | 0 | 0 | 0 | 0 | 0 | 0 | 0 | 0 |

TABLE 4

| Symptoms | Before eye drop initiation | | | On day 30 | | | On day 60 | | | On day 90 | | | On day 120 | | |
|---|---|---|---|---|---|---|---|---|---|---|---|---|---|---|---|
| Dose group | 1 | 2 | 3 | 1 | 2 | 3 | 1 | 2 | 3 | 1 | 2 | 3 | 1 | 2 | 3 |
| Number of eyes | 6 | 8 | 4 | 6 | 8 | 4 | 6 | 8 | 4 | 6 | 8 | 4 | 6 | 8 | 4 |
| Transparency | 6 | 8 | 4 | 6 | 8 | 0 | 6 | 8 | 0 | 0 | 0 | 0 | 0 | 0 | 0 |
| Formation of concentric circles | 0 | 0 | 0 | 0 | 2 | 4 | 0 | 0 | 0 | 4 | 8 | 0 | 2 | 8 | 1 |
| Distortion | 0 | 0 | 0 | 0 | 0 | 0 | 0 | 0 | 4 | 2 | 0 | 4 | 4 | 0 | 2 |
| Cortical opacity | 0 | 0 | 0 | 0 | 0 | 0 | 0 | 0 | 0 | 0 | 0 | 0 | 0 | 0 | 1 |

2. The eye drop experiments starting at 5 months since birth

A trace of concentric circles in one or two rings began to appear around lenses in the eyes of senile accelerated mice of age 5 months, but the transparency of their eyegrounds were judged good. As a result, they were temporarily judged to be transparent lenses before the initiation of eye drop.

The examination which was carried out on day 30 after the initiation of eye drop demonstrated the clear concentric circles in two lenses of Group 2 and four lenses of Group 3, but the eyes of Group 1 did not show any change.

The examination on day 60 after the initiation of eye drop demonstrated that Groups 1 and 2 showed good progress such that all eyes of the mice were judged transparent, and that formation of concentric circles accompanied with distortion were induced in four eyes of Group 3.

The examination on day 90 after the initiation of eye drop demonstrated concerning Groups 1 and 2, the occurrence of severe change inducing formation of concentric circles (in 12 eyes) and distortion (in 2 eyes). Of Group 3, four eyes were diagnosed to have distortion and intense change in the lenses thereof.

The examination on day 120 after the initiation of eye drop demonstrated the formation of concentric circles in all of the lenses of Groups 1 and 2 (14 lenses); in particular, the tendency of exacerbation accompanied by distortion was observed in 4 eyes of Group 1 (pyrenoxine administration group). On the other hand, of Group 3 as the control group, distortion disappeared in one of the four eyes accompanied by distortion. How- As is clearly demonstrated in Example 3, the effects on preventing or terminating the progress of cataract were observed in senile accelerated mice in Groups 1 and 2, compared with those of Group 3. Of the group given pyrenoxine solution along, however, there were observed a small number of mice in which cataract was in advanced stage. That is, the above effects are not necessarily designated absolute effects. On the contrary, of Group 2, namely the group given a combination of Fe solution and pyrenoxine solution, all the lenses remained transparent over a long period. Additionally to the above effects, there was obtained remarkable improving effects in that the lenses with severe symptoms such as cortical opacity recovered transparency.

In the above Example, even the other compounds except the compound (1—1), when administered, showed approximately identical effects as those described above.

The present invention is as has been described and thus, the agent of the present invention is excellent as an agent for preventing and treating opacity of lens.

We claim:

1. An opthalmic pharmaceutical composition for preventing and treating opacity of lens, comprising an effective amount to treat opacity of lens of the organic germanium compound represented by the formula;

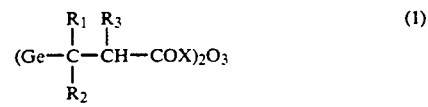

(1)

wherein R1 to R3 represent hydrogen atoms, lower alkyl groups each of which may be the same or different or phenyl groups substituted or unsubstituted; X represents a hydroxyl group, an O-lower alkyl group, an amino group or $O^-Y^\pm$ wherein Y represents a metal or a compound having a basic group and a pharmaceutically acceptable opthalmic carrier therefor.

2. An opthalmic pharmaceutical composition for preventing and treating opacity of lens, comprising an effective amount to prevent or treat opacity of lens of the organic germanium compound represented by the formula;

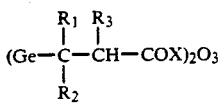 (1)

wherein R1 to R3 represent hydrogen atoms, lower alkyl groups each of which may be the same or different or phenyl groups substituted or unsubstituted; X represents a hydroxyl group, an O-lower alkyl group, an amino group or $O^-Y^\pm$ wherein Y represents a metal or a compound having a basic group and aminoguanidine and a pharmaceutically acceptable opthalmic carrier therefor.

3. The pharmaceutical composition for preventing and treating opacity of lens, according to claim 1 or 2, wherein the organic germanium compound represented by the formula (1) is the compound where R1 to R3 are hydrogen atoms, and X is a hydroxyl group.

4. The pharmaceutical composition for preventing and treating opacity of lens, according to claim 1, wherein the agent is prepared as an eye drop, together with a member selected from the group consisting of boric acid, sodium chloride, sodium hydroxide, benzalkonium chloride, ε-aminocaproic acid, methyl p-oxyaminobenzoic acid, chlorobutanol and combinations thereof.

5. An opthalmic pharmaceutical composition for preventing and treating opacity of lens, comprising an effective amount to prevent or treat opacity of lens of the organic germanium compound represented by the formula;

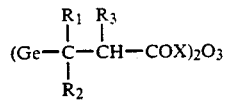 (1)

wherein R1 and R3 represent hydrogen atoms, lower alkyl groups each of which may be the same or different or phenyl groups substituted or unsubstituted; X represents a hydroxyl group, an O-lower alkyl group, an amino group, or $O^-Y^\pm$ wherein Y represents a metal or a compound having a basic group and a phenoxazine derivative and a pharmaceutically acceptable opthalmic carrier therefor.

6. The pharmaceutical composition for preventing and treating opacity of lens, according to claim 5, wherein the organic germanium compound represented by the formula (1) is the compound where R1 to R3 are hydrogen atoms, and X is hydroxyl group.

7. The pharmaceutical composition for preventing and treating opacity of lens, according to claim 5 or 6, wherein the phenoxazine derivative is represented by the formula;

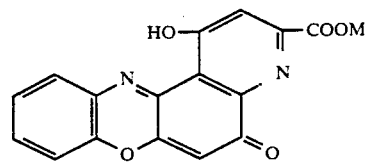

wherein M is a hydrogen atom or a metal.

8. The pharmaceutical composition for preventing and treating opacity of lens, according to claim 5, containing the sodium salt of the organic germanium compound or the sodium salt of the phenoxazine derivative or the sodium salt of both the organic germanium compound and the phenoxazine derivative.

9. The pharmaceutical composition for preventing and treating opacity of lens, according to claim 5, wherein the agent is prepared as an eye drop, together with a member selected from the group consisting of boric acid, sodium chloride, sodium hydroxide, benzalkonium chloride, ε-aminocaproic acid, methyl p-oxyaminobenzoic acid, chlorobutanol, and combinations thereof.

10. The pharmaceutical composition for preventing and treating opacity of lens, according to claim 5, wherein the organic germanium compound and the phenoxazine derivative are separately prepared into a formulation and the resulting formulation is mixed for use as needed.

11. A method for preventing and/or treating opacity of lens, comprising administering to humans in need of such treatment a therapeutically effective amount to prevent or treat opacity of lens of the organic germanium compound represented by the formula;

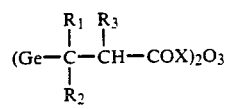 (1)

wherein R1 to R3 represent hydrogen atoms, lower alkyl groups each of which may be the same or different or phenyl groups substituted or unsubstituted; X represents a hydroxyl group, An O-lower alkyl group, an amino group or $O^-Y^\pm$ wherein Y represents a metal or a compound having a basic group.

12. A method for preventing and/or treating opacity of lens, comprising administering to human in need of such treatment a therapeutically effective amount to prevent or treat opacity of lens of the organic germanium compound represented by the formula;

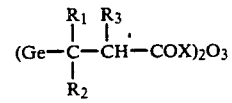 (1)

wherein R1 to R3 represent hydrogen atoms, lower alkyl groups each of which may b the same or different or phenyl groups substituted or unsubstituted; X represents a hydroxyl group, an O-lower alkyl group, an amino group, or $O^-Y^\pm$ wherein Y represents a metal or a compound having a basic group and aminoguanidine,.

13. The method for preventing and/or treating opacity of lens, according to claim 11 or 12, wherein the organic germanium compound represented by the formula (1) is the compound wherein $R_1$ to $R_3$ are hydrogen atoms, and X is a hydroxyl group.

14. The method for preventing and/or treating opacity of lens, according to claim 11, wherein an eye drop is prepared together with a member selected from the group consisting of boric acid, sodium chloride, sodium hydroxide, benzalkonium chloride, ε-aminocaproic acid, methyl p-oxyaminobenzoic acid, chlorobutanol and combinations thereof.

15. A method for preventing and/or treating opacity of lens, comprising administering to human in need of such treatment a therapeutically effective amount to prevent or treat opacity of lens of the organic germanium compound represented by the formula;

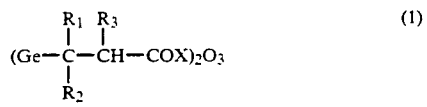

(1)

wherein R1 to R3 represent hydrogen atoms, lower alkyl groups each of which may be the same or different or phenyl groups substituted or unsubstituted; X represents a hydroxyl group, or $O^-Y^{\pm}$ wherein Y represents a metal or a compound having a basic group
and a phenoxazine derivative.

16. The method for preventing and/or treating opacity of lens, according to claim 15, wherein the organic germanium compound represented by the formula (1) is the compound where $R_1$ to $R_3$ are hydrogen atoms, and X is a hydroxyl group.

17. The method for preventing and/or treating opacity of lens, according to claim 15, wherein the phenoxazine derivative is represented by the formula;

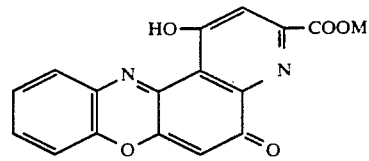

wherein M is a hydrogen atoms or a metal.

18. The method for preventing and/or treating opacity of lens, according to claim 15, containing the sodium salt of the organic germanium compound, the sodium salt of the phenoxazine derivative or the sodium salt of both the organic germanium compound and the phenoxazine derivative.

19. The method for preventing and/or treating opacity of lens, according to claim 15, wherein the organic germanium compound is prepared as an eye drop, together with a member selected from the group consisting of boric acid, sodium chloride, sodium hydroxide, benzalkonium chloride, ε-aminocaproic acid, methyl p-oxyaminobenzoic acid, chlorobutanol and combinations thereof.

20. The method for preventing and/or treating opacity of lens, according to claim 15, wherein the organic germanium compound and the phenoxazine derivative are separately prepared into a formulation and the resulting formulation is mixed for use as needed.

21. The pharmaceutical composition according to claim 1, wherein said lower alkyl group is methyl or ethyl.

22. The pharmaceutical composition according to claim 1, wherein said metal is sodium or potassium.

23. The pharmaceutical composition according to claim 1, wherein said compound having a basic group is lysozyme or basic amino acid.

24. The method according to claim 11, wherein said alkyl group is methyl or ethyl.

25. The method according to claim 11, wherein said metal is sodium or potassium.

26. The method according to claim 11, wherein said compound having a basic group is lysozyme or basic amino acid.

* * * * *